US012747481B2

(12) United States Patent
Dong et al.

(10) Patent No.: US 12,747,481 B2
(45) Date of Patent: Sep. 29, 2026

(54) PRIMER SETS AND MULTIPLEX DETECTION METHODS FOR SIMULTANEOUS QUALITATIVE AND QUANTITATIVE ANALYSIS OF EHP, DIV1, IHHNV, WSSV, AND VAHPND IN CRUSTACEANS

(71) Applicant: Yellow Sea Fisheries Research Institute, Chinese Academy Of Fishery Sciences, Qingdao (CN)

(72) Inventors: Xuan Dong, Qingdao (CN); Haoyu Lou, Qingdao (CN)

(73) Assignee: Yellow Sea Fisheries Research Institute, Chinese Academy Of Fishery Sciences, Qingdao (CN)

(*) Notice: Subject to any disclaimer, the term of this patent is extended or adjusted under 35 U.S.C. 154(b) by 0 days.

(21) Appl. No.: 19/241,564

(22) Filed: Jun. 18, 2025

(65) Prior Publication Data

US 2026/0117325 A1 Apr. 30, 2026

(30) Foreign Application Priority Data

Oct. 24, 2024 (CN) ......................... 202411487239.6

(51) Int. Cl.

| | |
|---|---|
| ***C12Q 1/6806*** | (2018.01) |
| ***C12Q 1/6848*** | (2018.01) |
| ***C12Q 1/6851*** | (2018.01) |
| ***C12Q 1/689*** | (2018.01) |
| ***C12Q 1/6895*** | (2018.01) |
| ***C12Q 1/70*** | (2006.01) |

(52) U.S. Cl.

CPC ........... *C12Q 1/701* (2013.01); *C12Q 1/6806* (2013.01); *C12Q 1/6848* (2013.01); *C12Q 1/6851* (2013.01); *C12Q 1/689* (2013.01); *C12Q 1/6895* (2013.01); *C12Q 2600/16* (2013.01)

(58) Field of Classification Search

None

See application file for complete search history.

(56) References Cited

U.S. PATENT DOCUMENTS

2020/0370094 A1 11/2020 Li

FOREIGN PATENT DOCUMENTS

| | | | |
|---|---|---|---|
| CN | 106636471 | A | 5/2017 |
| CN | 110396558 | A | 11/2019 |
| CN | 110616279 | A | 12/2019 |
| CN | 113897463 | A | 1/2022 |
| CN | 116162739 | A | 5/2023 |
| CN | 116287415 | A | 6/2023 |
| CN | 116694826 | A | 9/2023 |

OTHER PUBLICATIONS

Tey Putita Ou, Chanvannak Yun, et al. Improved detection of dengue and Zika viruses using multiplex RT-qPCR assays. Journal of Virological Methods. vol. 282. 2020. https://doi.org/10.1016/j.jviromet.2020.113862. (Year: 2020).*

Trisha R. Barnard, Alex B. Wang, Selena M. Sagan. A highly sensitive strand-specific multiplex RT-qPCR assay for quantitation of Zika virus replication. Journal of Virological Methods. vol. 307. 2022. https://doi.org/10.1016/j.jviromet.2022.114556. (Year: 2022).*

Yike Zhong, Yongxia Wang, Tong Zhao, et al. Multiplex real-time SYBR Green I PCR assays for simultaneous detection of 15 common enteric pathogens in stool samples. Molecular and Cellular Probes. vol. 53. 2020. https://doi.org/10.1016/j.mcp.2020.101619. (Year: 2020).*

Kishan Kishorchandra Kalaria, Girisha SK, Nithin MS, Puneeth TG, Suresh T, Taral Pravinkumar Vaghabhai and NA Pargi. Molecular detection of pathogens from cultured whiteleg shrimp farms in Karnataka, India. Int. J. Adv. Biochem. Res. 2024;8(3S):606-611. DOI: 10.33545/26174693.2024.v8.i3Sh.828 (Year: 2024).*

Giridharan,M. and Uma,A. Genbank accession No. KY674357.1. May 14, 2017. https://www.ncbi.nlm.nih.gov/nucleotide/KY674357.1 (Year: 2017).*

Salcedo,L., Durand,Y., Velazco,R., Pinto,J. and Rebaza,A. Genbank accession No. MW357695.1. Feb. 2, 2021. https://www.ncbi.nlm.nih.gov/nucleotide/MW357695.1 (Year: 2021).*

Lu,Y., Wu,C., Chen,I. and Tu,C. Genbank accession No. MW039594.1. Oct. 1, 2021. https://www.ncbi.nlm.nih.gov/nucleotide/MW039594.1 (Year: 2021).*

Jeon,H.J., Han,J.E. and Kim,J.H. Genbank accession No. CP083364.1. Sep. 20, 2021. https://www.ncbi.nlm.nih.gov/nucleotide/CP083364.1 (Year: 2021).*

Parrilla-Taylor,D.P., Vibanco-Perez,N., Duran-Avelar,M.J., Gomez-Gil,B., Llera-Herrera,R. and Vazquez-Juarez,R. Genbank accession No. MG432475.1. Aug. 20, 2021. https://www.ncbi.nlm.nih.gov/nucleotide/MG432475.1 (Year: 2021).*

Biotium. Fast EvaGreen qPCR Master Mix Product Information. Aug. 6, 2012. https://biotium.com/wp-content/uploads/2013/07/PI-31003.pdf (Year: 2012).*

(Continued)

*Primary Examiner* — Heather Calamita

(74) *Attorney, Agent, or Firm* — JEEN IP LAW, LLC

(57) ABSTRACT

A primer set and a detection method for simultaneous qualitative and quantitative detection of EHP, DIV1, IHHNV, WSSV, and $V_{AHPND}$, as well as their applications are provided, which belong to the technical field of pathogen detection. The specific sequences of the detection primer set are shown in SEQ ID NOs. 1-10. A kit and detection method containing the primer set is further provided. The detection primer set and detection method exhibit strong specificity, simple and convenient operation, short detection time, high sensitivity, and enable simultaneous qualitative and quantitative detection of the five pathogens EHP, DIV1, IHHNV, WSSV, and $V_{AHPND}$ in samples.

5 Claims, 7 Drawing Sheets

Specification includes a Sequence Listing.

(56) References Cited

OTHER PUBLICATIONS

Prediger, E. How to design primers and probes for PCR and qPCR. IDT. Apr. 8, 2024. https://www.idtdna.com/pages/education/decoded/article/designing-pcr-primers-and-probes (Year: 2024).*
Xuan Dong etc. ,Development of a Melting Curve-Based Triple Eva Green Real-Time PCR Assay for Simultaneous Detection of Three Shrimp Pathogens , «Animals» , vol. 14, Issue 4 , Feb. 11, 2024 , 592.
An Wei, etc., Establishment of Quadruple-Fluorescence Quantitative PCRDetection Method for WSSV, IHHNV, EHP and NHPB , «China Food Safety» , Issue 12 , pp. 99-101+106.
Ren Xue , etc., Investigation of Five Epidemic Pathogens From Penaeus Japonicus in Dalian «Journal of Aquaculture» , vol. 43, Issue 04 , pp. 23-29.

* cited by examiner

SEQUENCE LISTING

```
Sequence total quantity: 10
SEQ ID NO: 1           moltype = DNA  length = 23
FEATURE                Location/Qualifiers
source                 1..23
                       mol_type = other DNA
                       organism = synthetic construct
SEQUENCE: 1
cgagtttggc ggcacaattc tca                                   23

SEQ ID NO: 2           moltype = DNA  length = 25
FEATURE                Location/Qualifiers
source                 1..25
                       mol_type = other DNA
                       organism = synthetic construct
SEQUENCE: 2
tcctacaaat gctgtgtctg tgtaa                                 25

SEQ ID NO: 3           moltype = DNA  length = 20
FEATURE                Location/Qualifiers
source                 1..20
                       mol_type = other DNA
                       organism = synthetic construct
SEQUENCE: 3
ccaggcaagg tgggactccg                                       20

SEQ ID NO: 4           moltype = DNA  length = 20
FEATURE                Location/Qualifiers
source                 1..20
                       mol_type = other DNA
                       organism = synthetic construct
SEQUENCE: 4
tcgcgctcta agtgacggcg                                       20

SEQ ID NO: 5           moltype = DNA  length = 24
FEATURE                Location/Qualifiers
source                 1..24
                       mol_type = other DNA
                       organism = synthetic construct
SEQUENCE: 5
accgtggctc tcccagtcgg tggt                                  24

SEQ ID NO: 6           moltype = DNA  length = 24
FEATURE                Location/Qualifiers
source                 1..24
                       mol_type = other DNA
                       organism = synthetic construct
SEQUENCE: 6
gcgtgtgagg gggcaacggc gata                                  24

SEQ ID NO: 7           moltype = DNA  length = 25
FEATURE                Location/Qualifiers
source                 1..25
                       mol_type = other DNA
                       organism = synthetic construct
SEQUENCE: 7
cgcgagctag acggtgatga atggc                                 25

SEQ ID NO: 8           moltype = DNA  length = 22
FEATURE                Location/Qualifiers
source                 1..22
                       mol_type = other DNA
                       organism = synthetic construct
SEQUENCE: 8
atcagcccac gcagcgagtt ct                                    22
```

-continued

```
SEQ ID NO: 9            moltype = DNA  length = 20
FEATURE                 Location/Qualifiers
source                  1..20
                        mol_type = other DNA
                        organism = synthetic construct
SEQUENCE: 9
gggagatctt cgaaccctgg                                                  20

SEQ ID NO: 10           moltype = DNA  length = 20
FEATURE                 Location/Qualifiers
source                  1..20
                        mol_type = other DNA
                        organism = synthetic construct
SEQUENCE: 10
tgaatctcgg cacacactcg                                                  20
```

PRIMER SETS AND MULTIPLEX DETECTION METHODS FOR SIMULTANEOUS QUALITATIVE AND QUANTITATIVE ANALYSIS OF EHP, DIV1, IHHNV, WSSV, AND VAHPND IN CRUSTACEANS

CROSS-REFERENCE TO RELATED APPLICATIONS

This application claims priority to Chinese Patent Application No. 202411487239.6, filed on Oct. 24, 2024, which is hereby incorporated by reference in its entirety.

SEQUENCE LISTING

The present application contains a sequence listing which has been filed electronically in xml format and is hereby incorporated by reference in its entirety. Besides, a copy of the sequence listing in XML file is submitted later, the XML copy is created on Apr. 10, 2025, is named "Primer Sets and Multiplex Detection Methods for Simultaneous Qualitative and Quantitative Analysis of EHP, DIV1, IHHNV, WSSV, and $V_{AHPND}$ in Crustaceans-Sequence Listing" and is 12,288 bytes in size.

TECHNICAL FIELD

The present invention pertains to the technical field of pathogen detection. More specifically, it relates to primer sets, detection methods, and applications for simultaneous qualitative and quantitative analysis of EHP, DIV1, IHHNV, WSSV, and $V_{AHPND}$.

BACKGROUND

The aquaculture industry, as a critical component of global food production, has experienced rapid growth in recent years. Crustaceans, including economically significant species such as shrimp and crabs, hold substantial importance in this sector. However, the intensification of crustacean farming practices has led to escalating disease challenges, posing a major bottleneck to sustainable development. Pathogenic outbreaks not only cause mass mortality but also severely diminish economic returns.

Decapod iridescent virus 1 (DIV1) exhibits significant pathogenicity in shrimp and other crustaceans. Infected shrimp typically display marked pathological changes, including reduced vitality and high mortality rates. DIV1 outbreaks have caused substantial economic losses to the aquaculture industry, particularly in Asia, severely impacting shrimp production and quality. White spot syndrome virus (WSSV), highly contagious, can horizontally infect various crustaceans, including shrimp and crabs. Upon infection, the virus rapidly replicates within the host, leading to acute mortality. Infectious hypodermal and hematopoietic necrosis virus (IHHNV) infection often results in stunted growth and deformities in shrimp, significantly reducing aquaculture yields. IHHNV spreads both horizontally and vertically, infecting larvae and adult shrimp. Early-stage infections may lack obvious symptoms, but pathological severity escalates with viral replication. Acute hepatopancreatic necrosis disease (AHPND), primarily caused by *Vibrio* species carrying the pirAB gene, targets the shrimp hepatopancreas, inducing acute tissue necrosis. Infected shrimp exhibit symptoms like darkened body coloration, lethargy, and rapid mortality. *Enterocytozoon hepatopenaei* (EHP) predominantly infects the shrimp hepatopancreas. Transmission occurs via contaminated water, feed, or infected shrimp. Although EHP does not directly cause death, it severely retards growth, leading to economic losses for farmers. Recent trends show frequent co-infections by multiple pathogens, underscoring the urgent need for early rapid diagnostics, large-scale screening, and the development of multiplex detection methods targeting multiple pathogens simultaneously.

To address the recent emergence of co-infections by multiple pathogens in aquatic animals, multiplex fluorescent quantitative PCR has been developed. This technique combines the advantages of fluorescent quantitative detection technologies, including rapid processing, simple operation, high sensitivity, and specificity, while enabling simultaneous detection of multiple pathogens. It significantly reduces the time required for single-pathogen detection and represents a promising rapid multi-target detection approach. Despite these advantages, research on multiplex fluorescent quantitative PCR for rapid pathogen detection in aquatic animals remains in its infancy. Existing studies have primarily focused on multi-target detection in shrimp pathogens, leaving substantial gaps in crustacean pathogen detection. Particularly, there has been no reported multi-target detection technology capable of simultaneously identifying five major crustacean pathogens (EHP, DIV1, IHHNV, WSSV, and $V_{AHPND}$) to date.

SUMMARY

The objective of this invention is to overcome the limitations of existing technologies by providing a multiplex fluorescent quantitative PCR primer set and detection method capable of simultaneously identifying EHP, DIV1, IHHNV, WSSV, and $V_{AHPND}$. This approach demonstrates strong specificity, user-friendly operation, and clear differentiation between pathogens, offering a significant advancement in multi-target detection efficiency.

The present invention utilizes multiplex fluorescent quantitative PCR technology, targeting specific gene sequences of five pathogens: the SWP protein gene of EHP (GenBank accession number KX258197.1), the MCP protein gene of DIV1 (GenBank accession number KY681039.1), the NS1 protein gene of IHHNV (GenBank accession number JN616415.1), the WSV313 protein gene of WSSV (GenBank accession number NC_075105.1), and the PirB protein gene of $V_{AHPND}$ (GenBank accession number KM067908.1). Through the design, screening, and optimization of specific primers, a multiplex fluorescent quantitative detection method is established. Reaction conditions are optimized, and positive and negative control groups are incorporated during the process. Melting curve analysis is performed to ensure high accuracy, cost-effectiveness, rapidity, and sensitivity in detection, thereby achieving the objectives of the present invention.

The first objective of the present invention is to provide a primer set capable of simultaneous qualitative and quantitative detection of *Enterocytozoon hepatopenaei* (EHP), Decapod iridescent virus 1 (DIV1), infectious hypodermal and hematopoietic necrosis virus (IHHNV), white spot syndrome virus (WSSV), and *Vibrio* causing acute hepatopancreatic necrosis disease ($V_{AHPND}$). The detection primer set is as shown in SEQ ID NO. 1-10, with a specific sequence as follows:

```
                              (SEQ ID NO. 1)
EHP-2-F: CGAGTTTGGCGGCACAATTCTCA,

                              (SEQ ID NO. 2)
EHP-2-R: TCCTACAAATGCTGTGTCTGTGTAA;

                              (SEQ ID NO. 3)
IHHNV-P-3F: CCAGGCAAGGTGGGACTCCG,

                              (SEQ ID NO. 4)
IHHNV-P-3R: TCGCGCTCTAAGTGACGGCG;

                              (SEQ ID NO. 5)
DIV1-M-4F: ACCGTGGCTCTCCCAGTCGGTGGT,

                              (SEQ ID NO. 6)
DIV1-M-4R: GCGTGTGAGGGGGCAACGGCGATA;

                              (SEQ ID NO. 7)
VP-PB-3F: CGCGAGCTAGACGGTGATGAATGGC,

                              (SEQ ID NO. 8)
VP-PB-3R: ATCAGCCCACGCAGCGAGTTCT;

                              (SEQ ID NO. 9)
WSSV-Y-2F: GGGAGATCTTCGAACCCTGG,

                             (SEQ ID NO. 10)
WSSV-Y-2R: TGAATCTCGGCACACACTCG.
```

Second Objective: The second objective of this invention is to establish the application of the multiplex fluorescent quantitative primer set in simultaneous qualitative and quantitative detection of multiple pathogens, specifically EHP, DIV1, IHHNV, WSSV, and $V_{AHPND}$.

Third Objective: The third objective is to provide a multiplex fluorescent quantitative detection kit for simultaneous qualitative and quantitative analysis of these pathogens. The kit includes the aforementioned primer set as a core component.

Fourth Objective: The fourth objective is to develop a multiplex fluorescent quantitative detection method for simultaneous qualitative and quantitative identification of the pathogens EHP, DIV1, IHHNV, WSSV, and $V_{AHPND}$. The method comprises the following key steps:

(1) Sample Collection and Preparation: Collect samples and extract genomic DNA from the samples to serve as the template for fluorescent quantitative PCR. Use positive controls (samples confirmed to contain EHP, DIV1, IHHNV, WSSV, and $V_{AHPND}$) to validate the assay.

(2) Amplification Reaction Setup: Prepare the amplification reaction system by mixing the designed primer set with fluorescent quantitative premix and the extracted sample genomic DNA. Perform the fluorescent quantitative PCR amplification under optimized reaction conditions.

(3) Post-Amplification Analysis: After completing the amplification, conduct melting curve analysis to determine the presence or absence of EHP, DIV1, IHHNV, WSSV, and $V_{AHPND}$ in the samples. The distinct melting temperatures (Tm) of each pathogen-specific amplicon enable clear differentiation and confirmation of target pathogens.

The detection and interpretation of results through amplification curve analysis are performed as follows: The test is considered valid only if the negative control shows no amplification curve and the positive control exhibits a clear amplification curve with a Ct value≤37; otherwise, the test is invalid and must be repeated. A sample is determined positive for the presence of EHP, DIV1, IHHNV, WSSV, or $V_{AHPND}$ if its Ct value is ≤37. For samples with Ct values between 37 and 40, a retest is required by adding 2.5 μL of template DNA to the reaction system while proportionally reducing the volume of water. If the retested sample shows an amplification curve with a Ct value≤37, the result is confirmed as positive; otherwise, it is deemed negative. Samples without any amplification curve are directly classified as negative. This approach ensures accurate, reliable, and efficient simultaneous detection of the five target pathogens.

The detection of pathogens (EHP, DIV1, IHHNV, WSSV, and $V_{AHPND}$) via melting curve analysis is performed as follows: A single melting peak indicates the presence of a specific pathogen based on its Tm (melting temperature) value. For example: If the Tm matches the EHP-positive control, the sample contains EHP; If the Tm matches the WSSV-positive control, the sample contains WSSV; If the Tm matches the $V_{AHPND}$-positive control, the sample contains $V_{AHPND}$; If the Tm matches the IHHNV-positive control, the sample contains IHHNV; If the Tm matches the DIV1-positive control, the sample contains DIV1. Multiple melting peaks (two or more) indicate co-infection: Peaks corresponding to the Tm values of specific positive controls confirm the presence of those pathogens. No detectable peaks indicate the absence of all five pathogens (EHP, DIV1, IHHNV, WSSV, and $V_{AHPND}$) in the sample.

The fluorescent quantitative PCR reaction system has a total reaction volume of 25 μL, comprising the following components: 2×dsDNA-binding fluorescent dye premix (50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% (v/v) glycerol): 12.5 μL; Primers: EHP-2-F and EHP-2-R: 0.56 μM each; IHHNV-P-3F, IHHNV-P-3R, WSSV-Y-2F, and WSSV-Y-2R: 0.40 μM each; DIV1-M-4F, DIV1-M-4R, VP-PB-3F, and VP-PB-3R: 0.32 μM each; Genomic DNA template: 1 μL; Deionized water: Added to adjust the total volume to 25 μL.

The optimized reaction conditions for the fluorescent quantitative PCR are as follows: Initial Denaturation: 95° C. for 3 minutes; Amplification Cycles (40 cycles): Denaturation: 95° C. for 10 seconds, Annealing: 64° C. for 20 seconds; Melting Curve Analysis: Denaturation: 95° C. for 15 seconds, Hybridization: 64° C. for 1 minute, Ramp: Gradually increase temperature from 68° C. to 85° C. to collect melting curve data.

The present invention demonstrates superior benefits by designing specific primer sets targeting the following pathogen-specific gene sequences: the SWP protein gene of EHP (GenBank accession no. KX258197.1), the MCP protein gene of DIV1 (GenBank accession no. KY681039.1), the NS1 protein gene of IHHNV (GenBank accession no. JN616415.1), the WSV313 protein gene of WSSV (GenBank accession no. NC_075105.1), and the PirB protein gene of $V_{AHPND}$ (GenBank accession no. KM067908.1). These primers exhibit high specificity and enable simultaneous detection of EHP, DIV1, IHHNV, WSSV, and $V_{AHPND}$ in a single assay. The invention further establishes a screened primer set and a robust detection protocol to accurately determine the presence or absence of these pathogens in samples. The primer set and method developed herein offer strong specificity, user-friendly operation, rapid detection, high sensitivity, and the ability to detect five pathogens concurrently (EHP, DIV1, IHHNV, WSSV, and $V_{AHPND}$). This innovation is particularly suitable for multiplex pathogen screening in aquaculture facilities and holds broad application prospects in the field.

DESCRIPTION OF EMBODIMENTS

Figure 1:
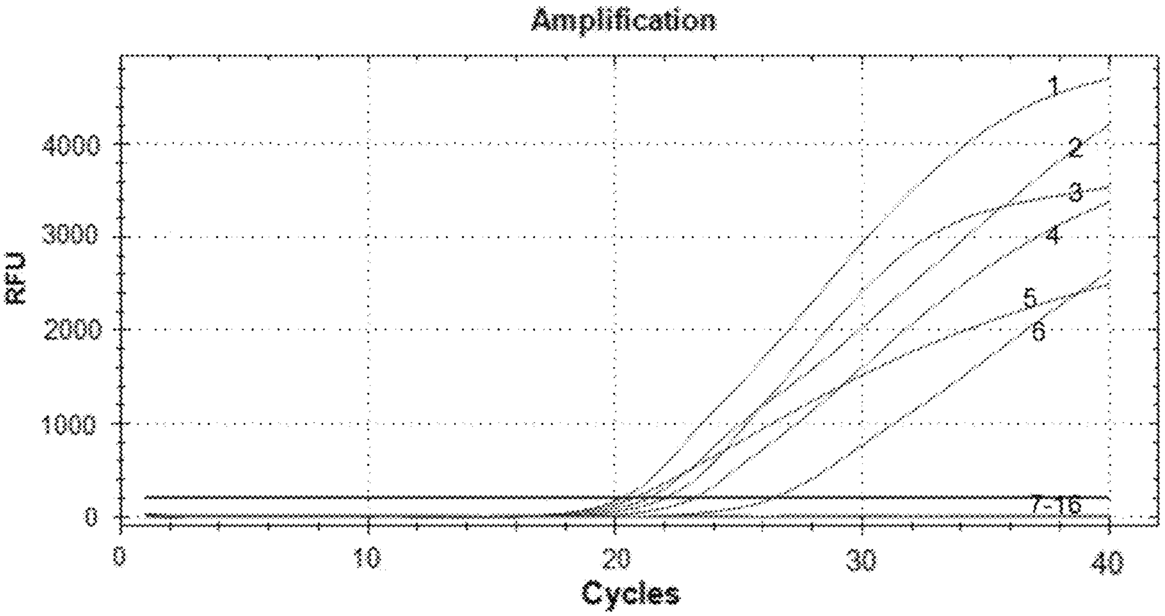
FIG. 1 shows the amplification curve results from the specificity experiment: 1: Mixed solution containing recombinant plasmids of EHP, DIV1, IHHNV, WSSV, and $V_{AHPND}$; 2: EHP; 3: DIV1; 4: IHHNV; 5: WSSV; 6: $V_{AHPND}$; 7: *Vibrio orientalis;* 8*: Photobacterium damselae* subsp. *piscicida,* 9: *Vibrio rotiferianus;* 10: cDNA of yellow head virus genotype 8 (YHV-8); 11: cDNA of infectious myonecrosis virus (IMNV); 12: cDNA of covert mortality nodavirus (CMNV); 13: cDNA of infectious precocity virus (IPV); 14: cDNA of Taura syndrome virus (TSV); 15: cDNA of Macrobrachium *rosenbergii* golda virus (MrGV); 16: Ultrapure water.

The following embodiments are further explanations of the present disclosure, do not make limitations to the present disclosure.

Example 1: Design and Synthesis of Primers

Following the principles of fluorescent quantitative PCR primer design, target gene sequences suitable for fluorescent amplification were identified in the GenBank database for the pathogens EHP, DIV1, IHHNV, WSSV, and $V_{AHPND}$. The following highly specific sequences were selected as targets: EHP: Gene sequence encoding the SWP protein (GenBank accession no. KX258197.1); DIV1: Gene sequence encoding the MCP protein (GenBank accession no. KY681039.1); IHHNV: Gene sequence encoding the NS1 protein (GenBank accession no. JN616415.1); WSSV: Gene sequence encoding the WSV313 protein (GenBank accession no. NC_075105.1); $V_{AHPND}$: Gene sequence encoding the PirB protein (GenBank accession no. KM067908.1). Based on conserved regions within these target genes and adhering to real-time quantitative PCR (qPCR) primer design guidelines, multiple primer sets were designed using the National Center for Biotechnology Information (NCBI) tools. After rigorous screening, a primer set demonstrating optimal specificity and amplification efficiency was selected for subsequent validation and application. The detection primer set is as shown in SEQ ID NO. 1-10, with a specific sequence as follows:

```
                                          (SEQ ID NO. 1)
EHP-2-F: CGAGTTTGGCGGCACAATTCTCA,

                                          (SEQ ID NO. 2)
EHP-2-R: TCCTACAAATGCTGTGTCTGTGTAA;

                                          (SEQ ID NO. 3)
IHHNV-P-3F: CCAGGCAAGGTGGGACTCCG,

                                          (SEQ ID NO. 4)
IHHNV-P-3R: TCGCGCTCTAAGTGACGGCG;

                                          (SEQ ID NO. 5)
DIV1-M-4F: ACCGTGGCTCTCCCAGTCGGTGGT,

                                          (SEQ ID NO. 6)
DIV1-M-4R: GCGTGTGAGGGGGCAACGGCGATA;

                                          (SEQ ID NO. 7)
VP-PB-3F: CGCGAGCTAGACGGTGATGAATGGC,

                                          (SEQ ID NO. 8)
VP-PB-3R: ATCAGCCCACGCAGCGAGTTCT;

                                          (SEQ ID NO. 9)
WSSV-Y-2F: GGGAGATCTTCGAACCCTGG,

                                         (SEQ ID NO. 10)
WSSV-Y-2R: TGAATCTCGGCACACACTCG.
```

Example 2: Nucleic Acid Extraction

For tissue samples containing EHP, DIV1, IHHNV, WSSV, $V_{AHPND}$, *Vibrio orientalis, Photobacterium damselae* subsp. *piscicida*, or *Vibrio rotiferianus*, genomic DNA was extracted using a DNA extraction kit and served as the template for fluorescent quantitative PCR. For tissue samples containing IMNV, CMNV, YHV-8, IPV, TSV, or MrGV, viral genomic RNA was extracted using a viral RNA extraction kit, followed by reverse transcription using a reverse transcription kit to generate cDNA as the template for fluorescent quantitative PCR. This protocol ensures appropriate nucleic acid preparation for both DNA and RNA viruses, enabling accurate and reliable detection across diverse pathogen types.

Example 3: Construction of SWP, MCP, NS1, WSV313, and PirB Recombinant Plasmids

Recombinant plasmids containing the gene sequences corresponding to the SWP protein of EHP, the MCP protein of DIV1, the NS1 protein of IHHNV, the WSV313 protein of WSSV, and the PirB protein of $V_{AHPND}$ were constructed as follows: Using the pUC57 vector, the target DNA fragments (SWP, MCP, NS1, WSV313, and PirB gene sequences) were individually ligated into pUC57 via DNA ligase, generating recombinant plasmids pUC57-swp, pUC57-mcp, pUC57-ns1, pUC57-wsv313, and pUC57-pirB. These plasmids were transformed into *E. coli* DH5α competent cells. Positive clones were selected using ampicillin at a final concentration of 100 μg/mL. Recombinant plasmid DNA was extracted using a plasmid extraction kit, and successful construction was confirmed by PCR and sequencing.

Example 4: Specificity of the qPCR Method

The reaction system for fluorescent quantitative PCR has a total volume of 25 μL, containing: 2×dsDNA-binding fluorescent dye premix (50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% (v/v) glycerol): 12.5 μL; Primers: EHP-2-F and EHP-2-R (0.56 μM each); IHHNV-P-3F, IHHNV-P-3R, WSSV-Y-2F, and WSSV-Y-2R (0.40 μM each); DIV1-M-4F, DIV1-M-4R, VP-PB-3F, and VP-PB-3R (0.32 μM each); Genomic DNA template: 1 μL; Deionized water: Added to adjust the total volume to 25 μL.

After thorough mixing, the reaction mixture was loaded into a real-time PCR instrument under the following conditions: Initial denaturation: 95° C. for 3 minutes; Amplification cycles (40 cycles): 95° C. for 10 seconds (denaturation), 64° C. for 20 seconds (annealing); Melting curve analysis: 95° C. for 15 seconds, 64° C. for 1 minute, followed by a temperature ramp from 68° C. to 85° C. to collect melting curve data.

Figure 2:
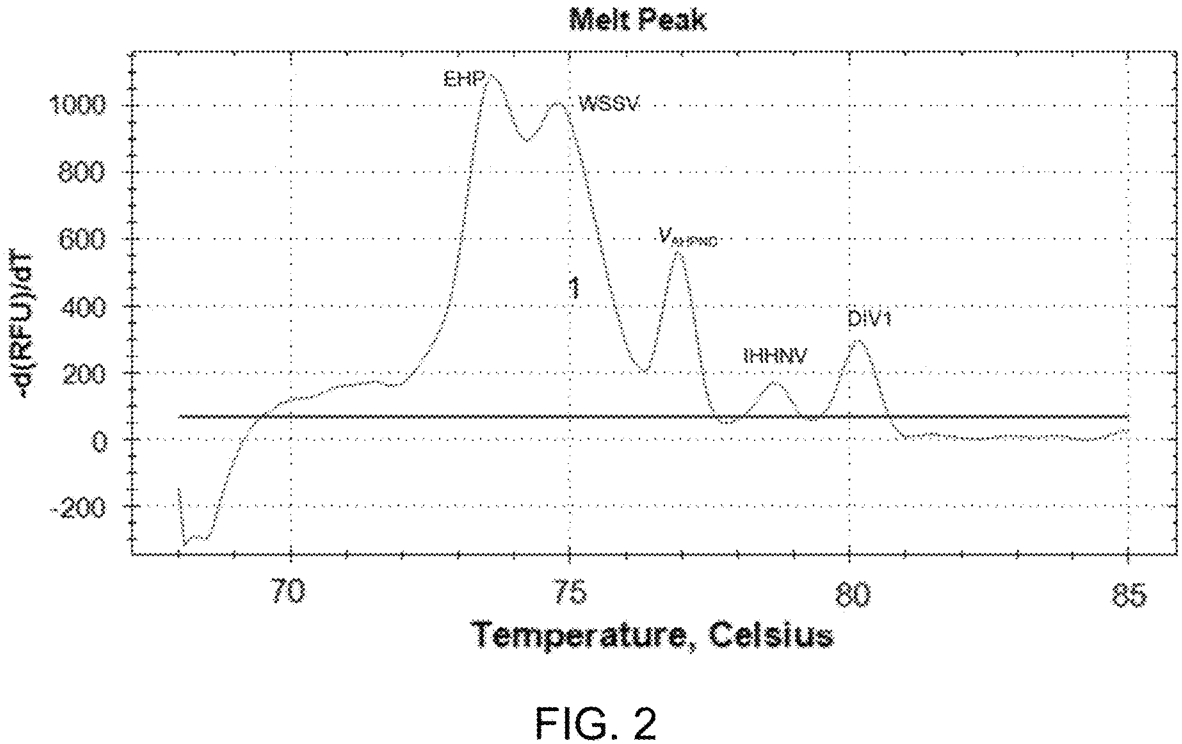
FIG. 2 shows the melting curve results from the specificity experiment: 1: Mixed solution containing recombinant plasmids of EHP, DIV1, IHHNV, WSSV, and $V_{AHPND}$.

As shown in FIGS. 1 and 2, the presence of pathogens was determined based on melting curve characteristics: Single peak with matching Tm value: EHP: Peak Tm matches the EHP-positive control; WSSV: Peak Tm matches the WSSV-positive control; $V_{AHPND}$: Peak Tm matches the $V_{AHPND}$-positive control; IHHNV: Peak Tm matches the IHHNV-positive control; DIV1: Peak Tm matches the DIV1-positive control. Multiple peaks: Co-infection is confirmed if peaks correspond to Tm values of specific positive controls. No peaks: The sample is negative for all five pathogens (EHP, DIV1, IHHNV, WSSV, and $V_{AHPND}$).

Example 5: Sensitivity of the qPCR Method

The recombinant plasmids pUC57-swp, pUC57-mcp, pUC57-ns1, pUC57-wsv313, and pUC57-pirB were diluted to a uniform concentration of 100 ng/μL, followed by serial 10-fold dilutions using $ddH_2O$ to generate templates ranging from $1\times10^8$-$1\times10^1$ copies/μL. These dilutions served as DNA templates for sensitivity testing in the fluorescent quantitative assay.

The fluorescent quantitative reaction system (25 μL total volume) comprised: 2×dsDNA-binding fluorescent dye premix (50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% (v/v) glycerol): 12.5 μL; Primers: EHP-2-F and EHP-2-R (0.56 μM each); IHHNV-P-3F, IHHNV-P-3R, WSSV-Y-2F, and WSSV-Y-2R (0.40 μM each); DIV1-M-4F, DIV1-M-4R, VP-PB-3F, and VP-PB-3R (0.32 μM each); Genomic DNA template: 1 μL; Deionized water: Added to adjust the total volume to 25 μL.

The reaction mixture was thoroughly mixed and subjected to the following thermal cycling conditions in a real-time PCR instrument: Initial denaturation: 95° C. for 3 minutes; Amplification cycles (40 cycles): 95° C. for 10 seconds (denaturation), 64° C. for 20 seconds (annealing); Melting curve analysis: 95° C. for 15 seconds, 64° C. for 1 minute, followed by a temperature ramp from 68° C. to 85° C. to collect melting curve data.

Figure 3:
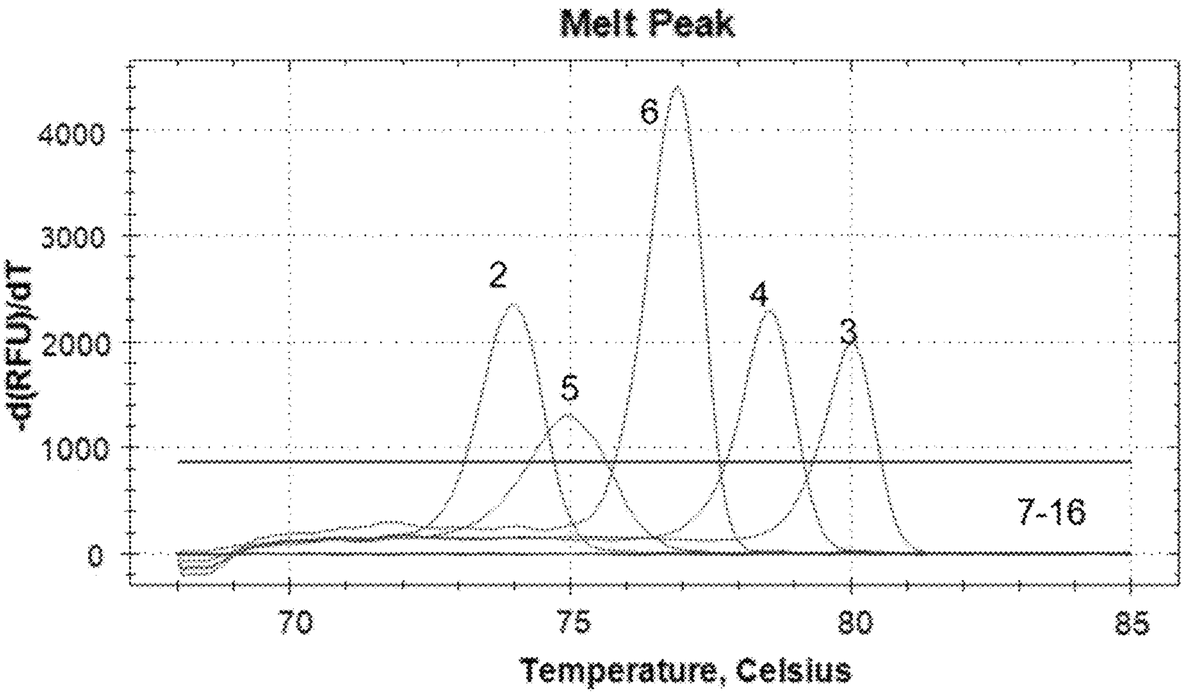
FIG. 3 displays the melting curve results from the specificity experiment: 2: EHP; 3: DIV1; 4: IHHNV; 5: WSSV; 6: $V_{AHPND}$; 7: *Vibrio orientalis;* 8*: Photobacterium damselae* subsp. *piscicida,* 9: *Vibrio rotiferianus;* 10: cDNA of Yellow Head Virus genotype 8 (YHV-8); 11: cDNA of infectious myonecrosis virus (IMNV); 12: cDNA of covert mortality nodavirus (CMNV); 13: cDNA of infectious precocity virus (IPV); 14: cDNA of Taura syndrome virus (TSV); 15: cDNA of Macrobrachium *rosenbergii* golda virus (MrGV); 16: Ultrapure water.
Figure 4A:
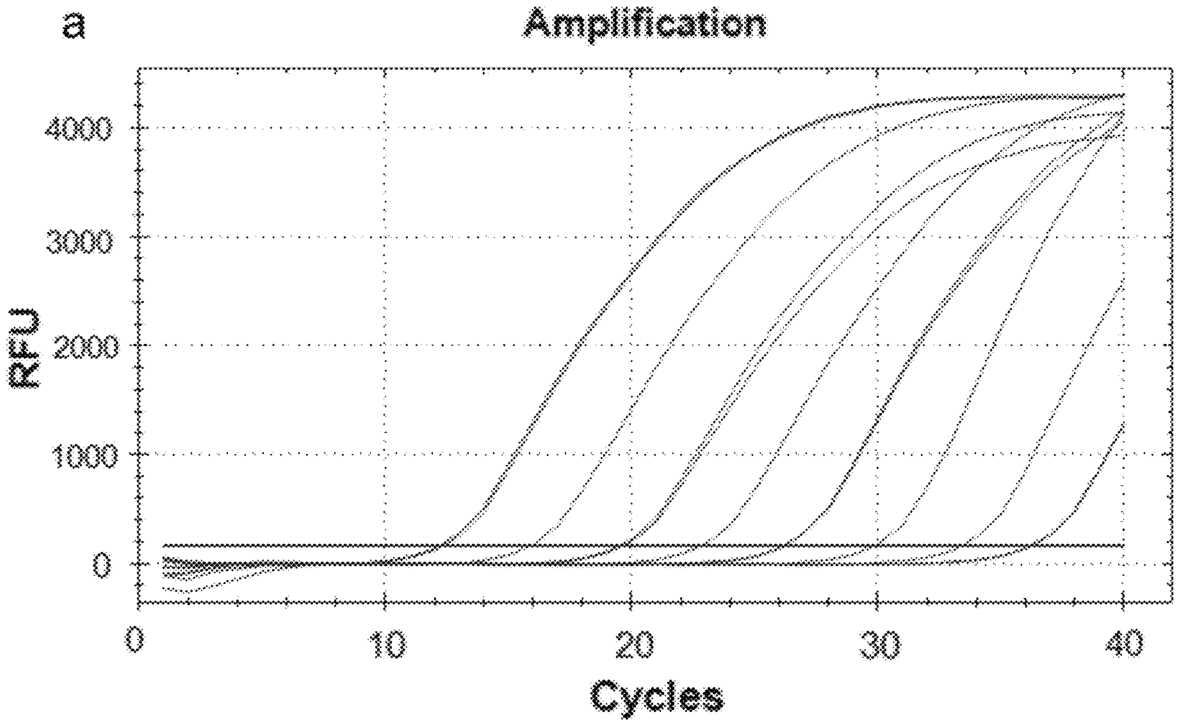
FIG. 4*a* presents the amplification curves and standard curves for recombinant plasmids containing the SWP protein gene sequence of EHP ($1\times10^1$-$1\times10^8$ copies/μL).
Figure 4B:
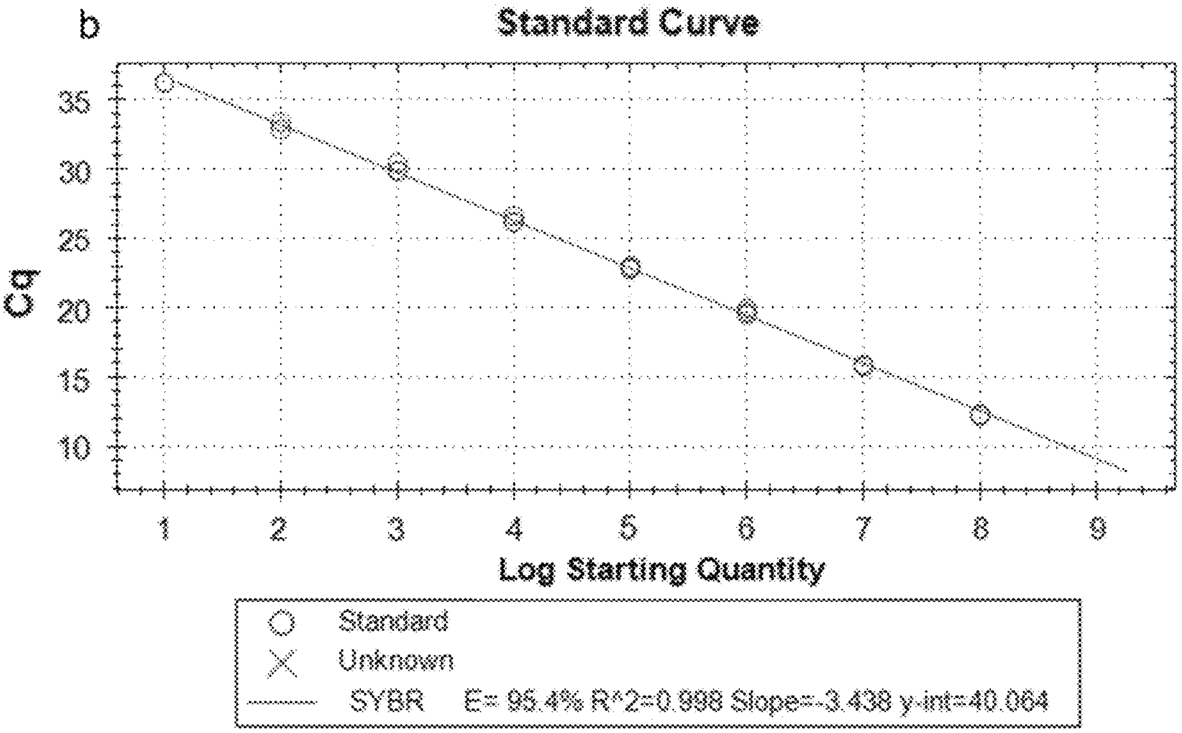
FIG. 4*b* presents the standard curves for recombinant plasmids containing the SWP protein gene sequence of EHP ($1\times10^1$-$1\times10^8$ copies/μL).
Figure 4C:
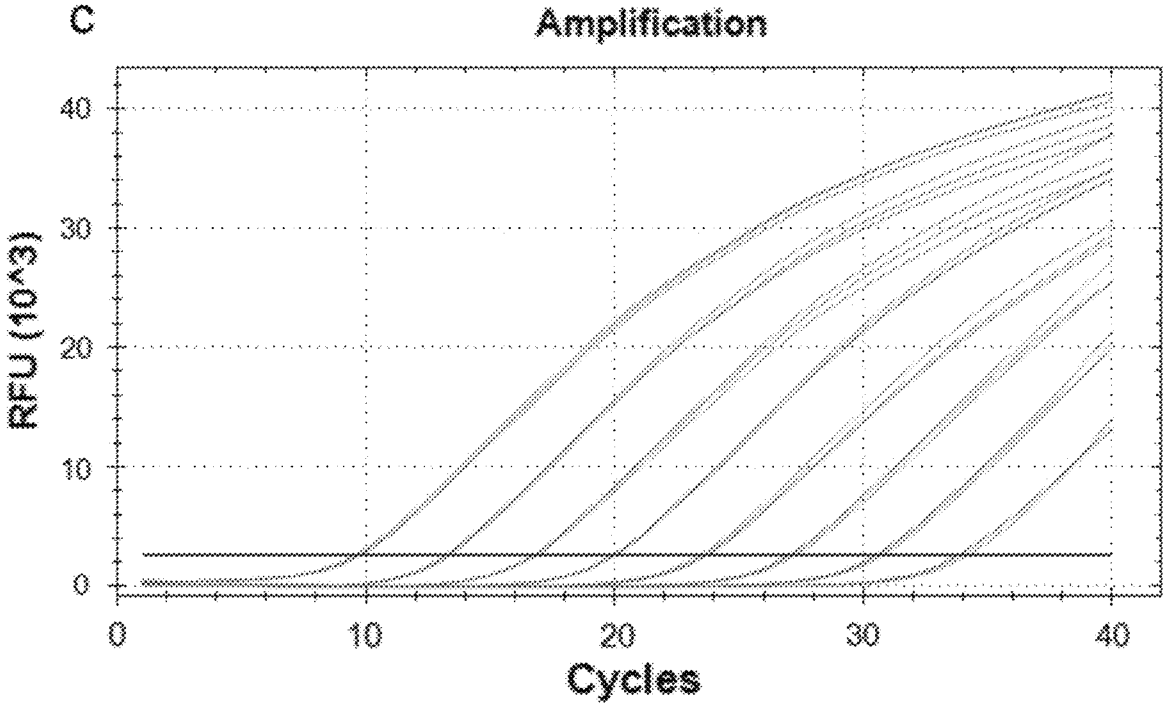
FIG. 4*c* presents the amplification curves for recombinant plasmids containing the WSV313 protein gene sequence of WSSV ($1\times10^1$-$1\times10^8$ copies/μL).
Figure 4D:
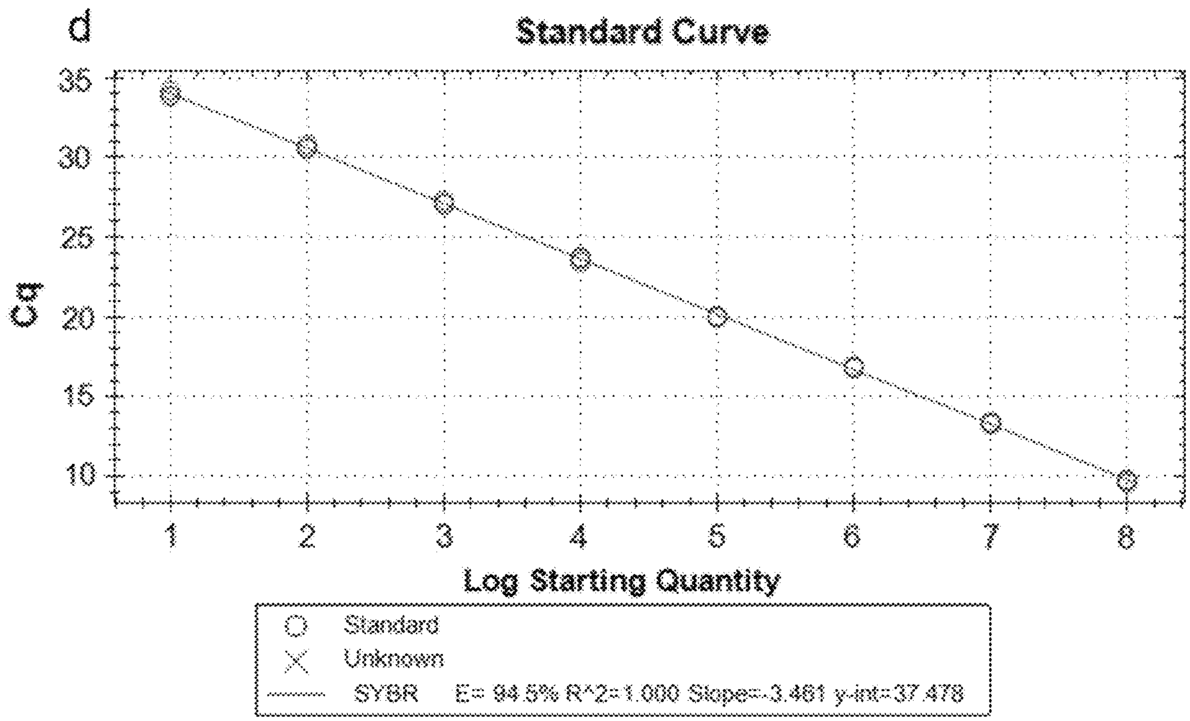
FIG. 4*d* presents the standard curves for recombinant plasmids containing the WSV313 protein gene sequence of WSSV ($1\times10^1$-$1\times10^8$ copies/μL).
Figure 4E:
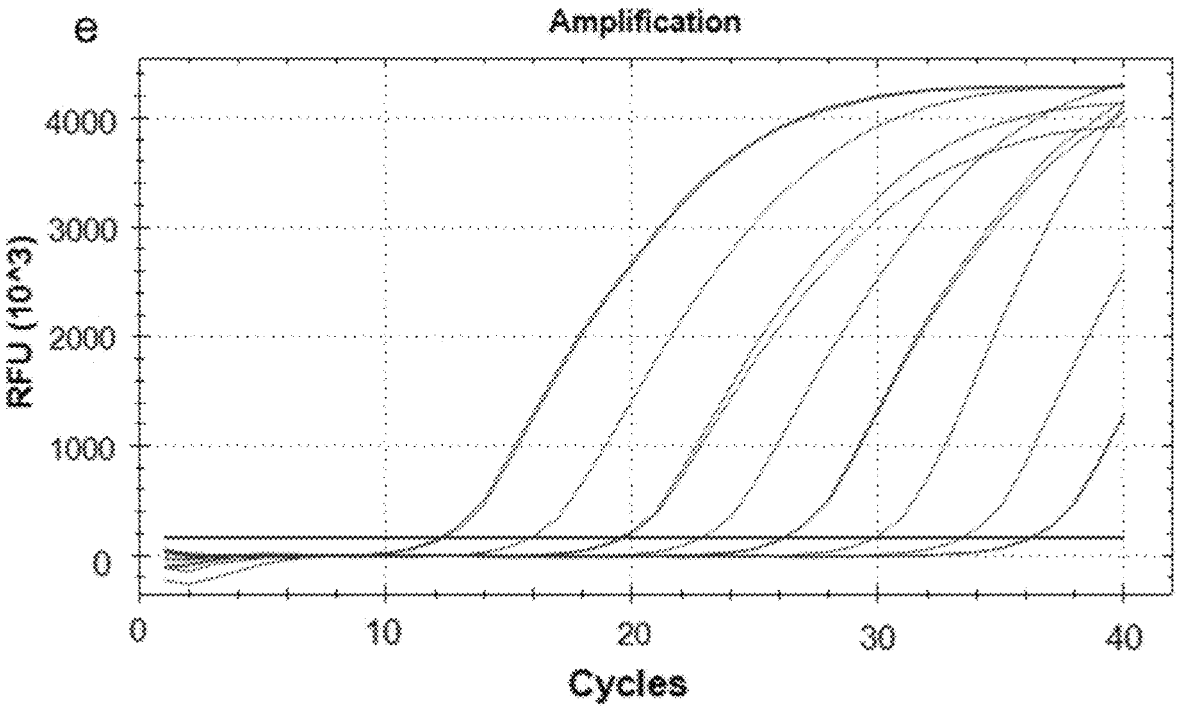
FIG. 4*e* presents the amplification curves for recombinant plasmids containing the NS1 protein gene sequence of IHHNV ($1\times10^1$-$1\times10^8$ copies/μL).
Figure 4F:
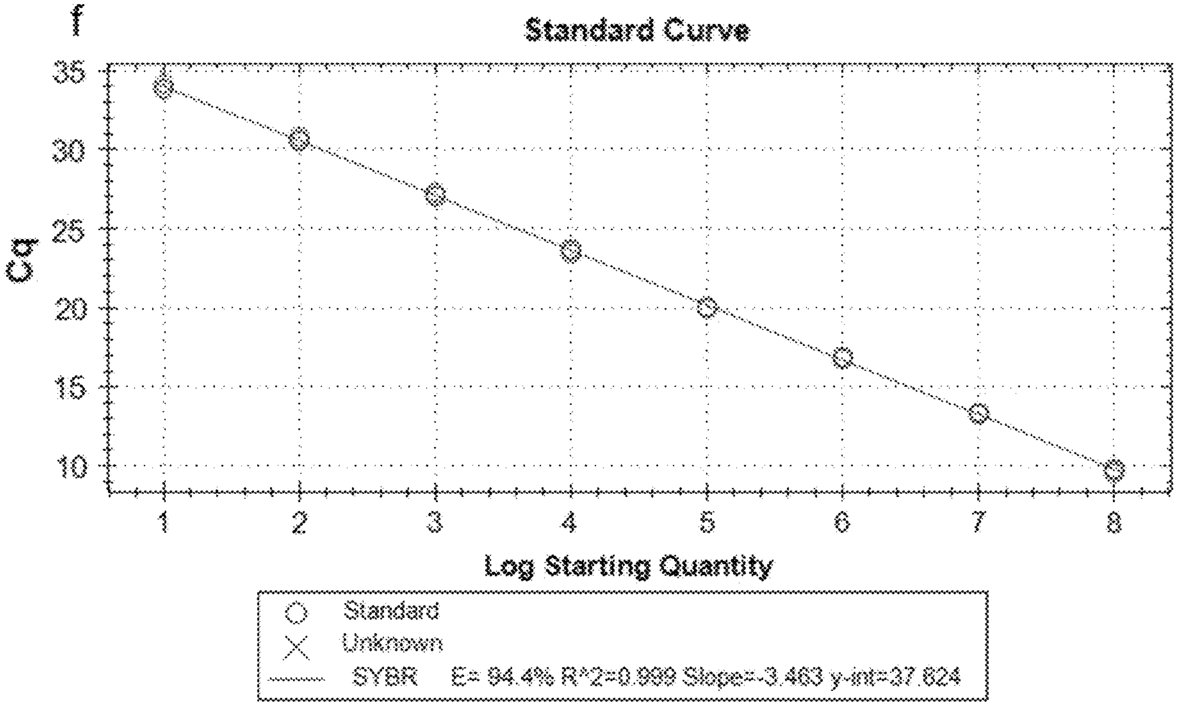
FIG. 4*f* presents the standard curves for recombinant plasmids containing the NS1 protein gene sequence of IHHNV ($1\times10^1$-$1\times10^8$ copies/μL).
Figure 4G:
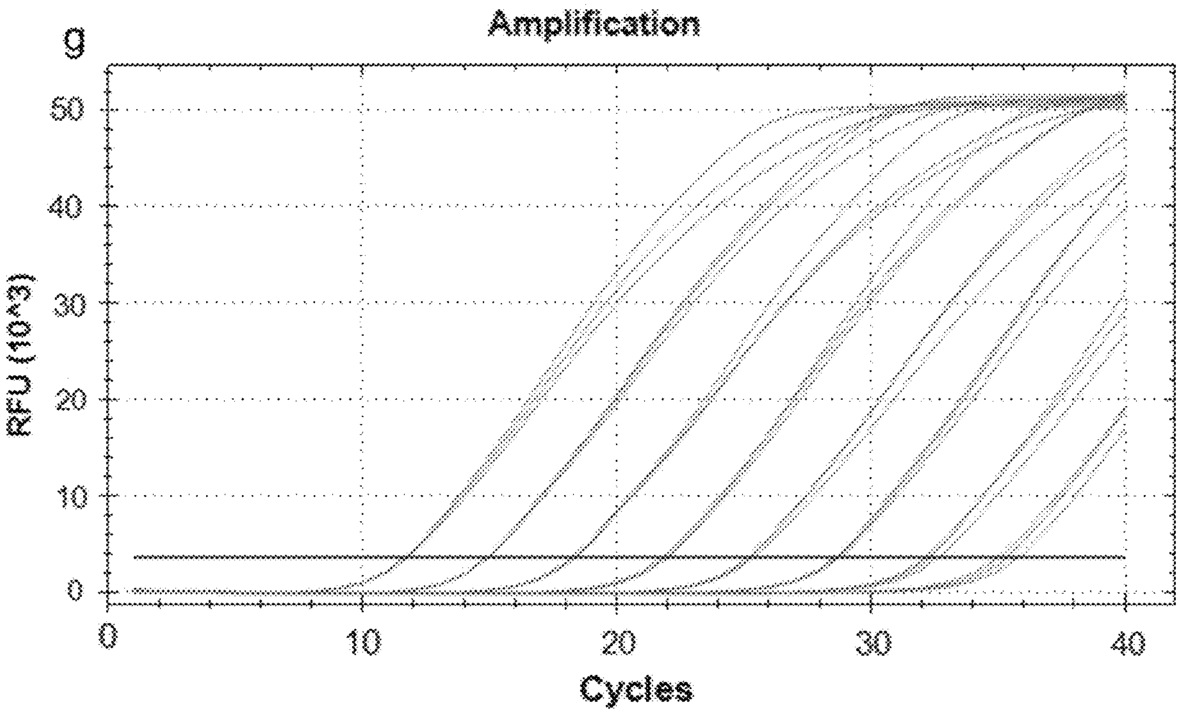
FIG. 4*g* presents the amplification curves for recombinant plasmids containing the PirB protein gene sequence of $V_{AHPND}$ ($1\times10^1$-$1\times10^8$ copies/μL).
Figure 4H:
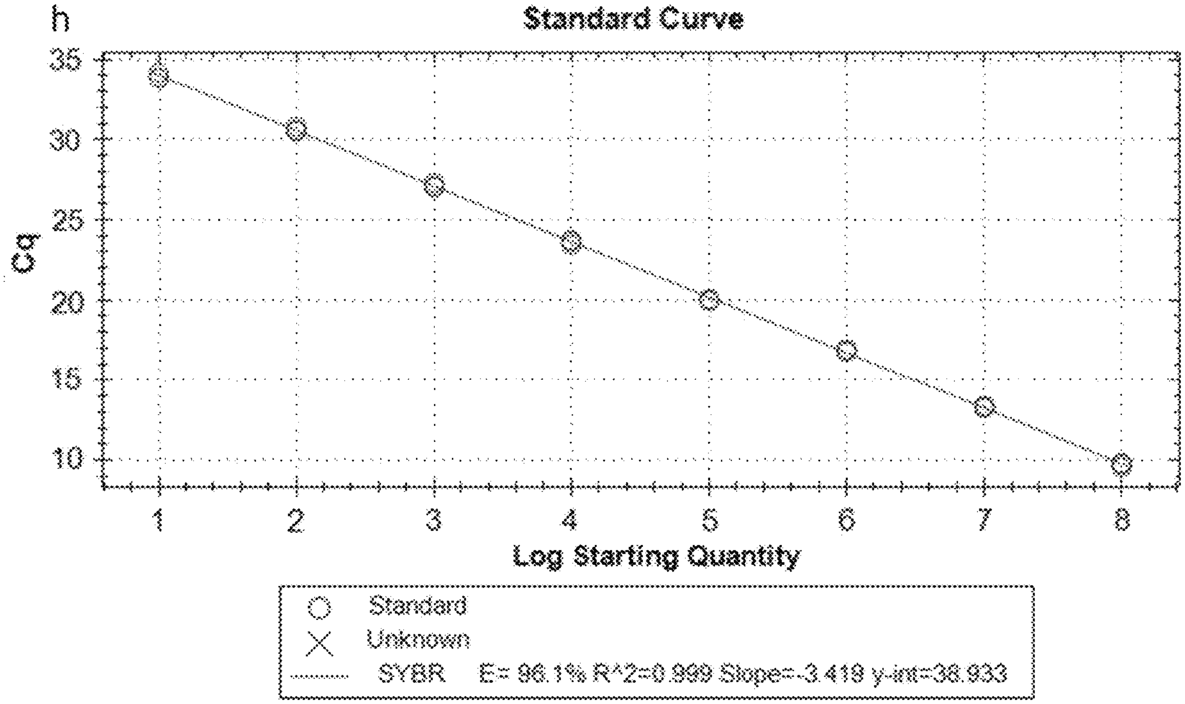
FIG. 4*h* presents the standard curves for recombinant plasmids containing the PirB protein gene sequence of $V_{AHPND}$ ($1\times10^1$-$1\times10^8$ copies/μL).
Figure 4I:
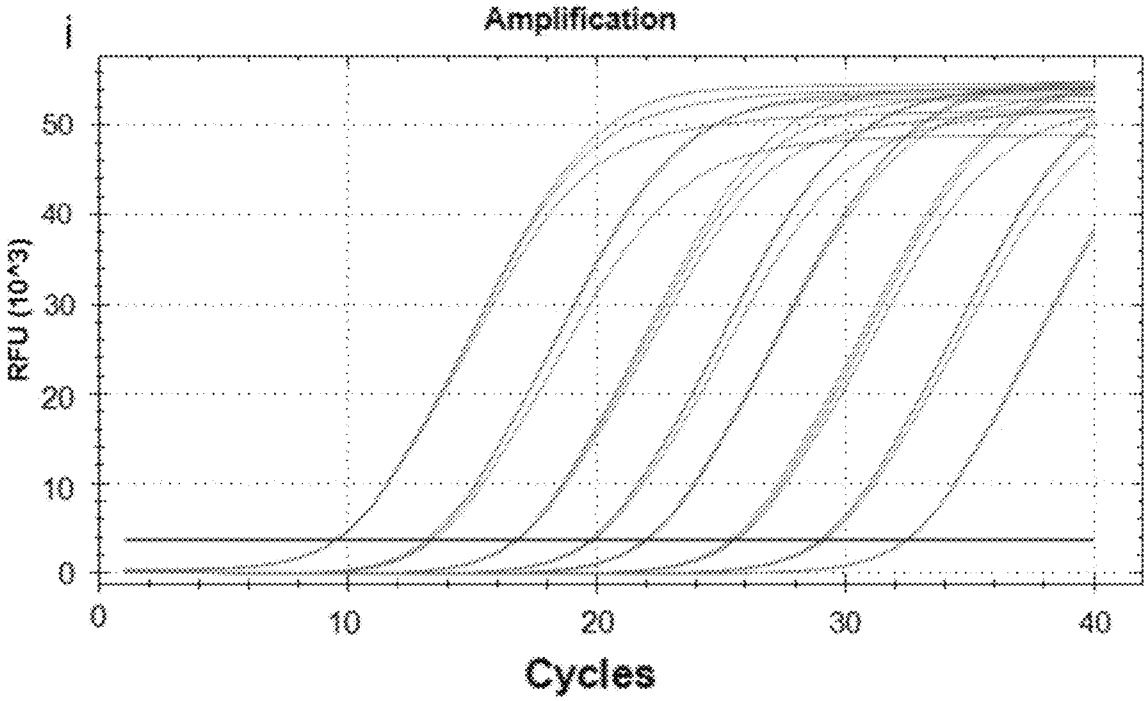
FIG. 4*i* presents the amplification curves for recombinant plasmids containing the MCP protein gene sequence of DIV1 ($1\times10^1$-$1\times10^8$ copies/μL).
Figure 4J:
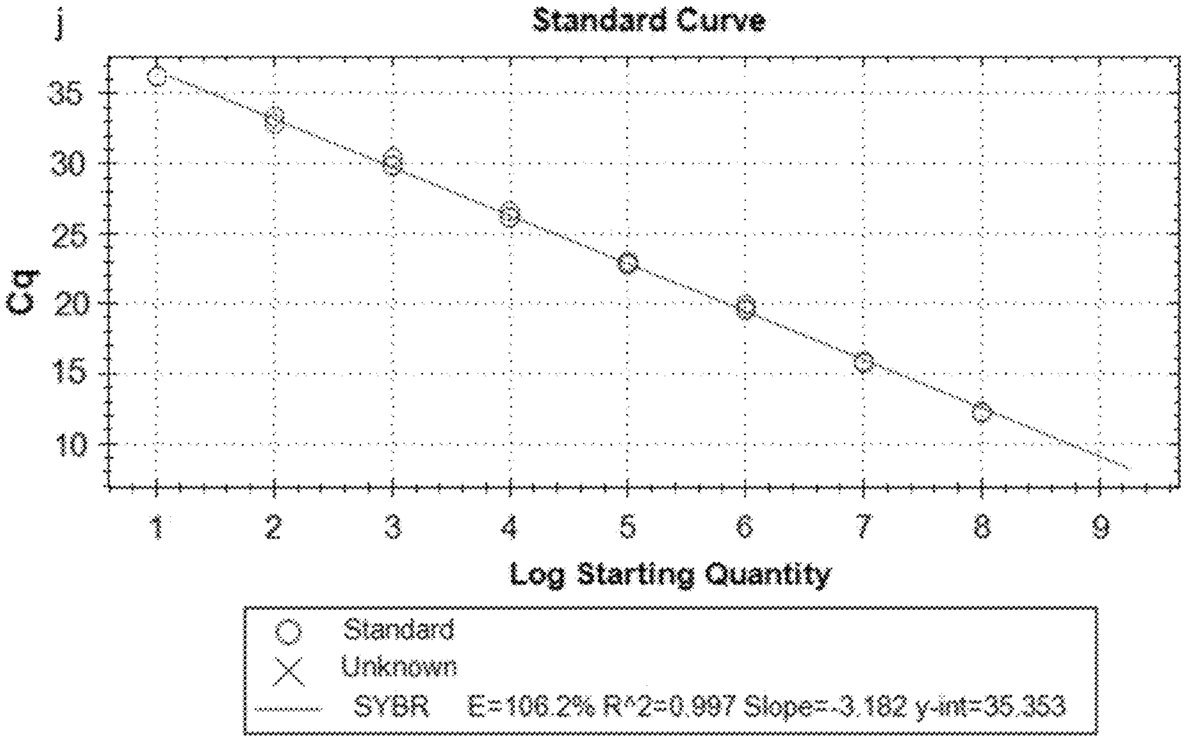
FIG. 4*j* presents the standard curves for recombinant plasmids containing the MCP protein gene sequence of DIV1 ($1\times10^1$-$1\times10^8$ copies/μL).

As shown in FIGS. 3 and 4, the sensitivity of the developed fluorescent quantitative method reached $1\times10^1$ copies/μL. These results demonstrate that the multiplex fluorescent quantitative detection method achieves a sensitivity of $1\times10^1$ copies/μL, confirming its capability to detect low-abundance pathogen targets with high precision.

Example 6: Repeatability of the qPCR Method

The recombinant plasmids pUC57-swp, pUC57-mcp, pUC57-ns1, pUC57-wsv313, and pUC57-pirB were diluted to a uniform concentration of 100 ng/μL and further subjected to 10-fold serial dilutions using $ddH_2O$ to generate DNA templates at concentrations of $1\times10^8$ copies/μL, $1\times10^7$ copies/μL, $1\times10^6$ copies/μL, $1\times10^5$ copies/μL, $1\times10^4$ copies/μL, $1\times10^3$ copies/μL, $1\times10^2$ copies/μL, and $1\times10^1$ copies/μL for repeatability evaluation in the fluorescent quantitative assay.

The fluorescent quantitative reaction system (25 μL total volume) included: 2×dsDNA-binding fluorescent dye premix (50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% (v/v) glycerol: 12.5 μL; Primers: EHP-2-F and EHP-2-R (0.56 μM each); IHHNV-P-3F, IHHNV-P-3R, WSSV-Y-2F, and WSSV-Y-2R (0.40 μM each); DIV1-M-4F, DIV1-M-4R, VP-PB-3F, and VP-PB-3R (0.32 μM each); Genomic DNA template: 1 μL; Deionized water: Added to adjust the total volume to 25 μL.

Each group included three technical replicates, and the experiment was repeated across three independent batches. Both inter-group variation (variation among replicates within a single batch) and inter-batch variation (variation across different experimental batches) were analyzed. The results showed that both inter-group and inter-batch variations were less than 3%, confirming the high reproducibility of the method.

Example 7: Accuracy of the qPCR Method

For tissue samples containing EHP, DIV1, IHHNV, WSSV, $V_{AHPND}$, *Vibrio orientalis, Photobacterium damselae* subsp. *piscicida*, or *Vibrio rotiferianus*, genomic DNA was extracted using a DNA extraction kit and served as the template for fluorescent quantitative PCR. For tissue samples containing IMNV, CMNV, YHV-8, IPV, TSV, or MrGV, viral genomic RNA was extracted using a viral RNA extraction kit, followed by reverse transcription using a reverse transcription kit to generate cDNA as the template for fluorescent quantitative PCR.

The fluorescent quantitative reaction system (25 μL total volume) comprised: 2×dsDNA-binding fluorescent dye premix (50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% (v/v) glycerol): 12.5 μL; Primers: EHP-2-F and EHP-2-R (0.56 M each); IHHNV-P-3F, IHHNV-P-3R, WSSV-Y-2F, and WSSV-Y-2R (0.40 μM each); DIV1-M-4F, DIV1-M-4R, VP-PB-3F, and VP-PB-3R (0.32 μM each); Genomic DNA template: 1 μL; Deionized water: Added to adjust the total volume to 25 μL.

The reaction mixture was thoroughly mixed and subjected to the following thermal cycling conditions in a real-time PCR instrument: Initial denaturation: 95° C. for 3 minutes; Amplification cycles (40 cycles): 95° C. for 10 seconds (denaturation), 64° C. for 20 seconds (annealing); Melting curve analysis: 95° C. for 15 seconds, 64° C. for 1 minute, followed by a temperature ramp from 68° C. to 85° C. to collect melting curve data.

The results were compared with those obtained using WOAH-recommended fluorescent quantitative methods for the five pathogens. The detection outcomes were fully consistent, confirming the reliability and accuracy of this method. By analyzing melting curves, the presence of EHP, DIV1, IHHNV, WSSV, or $V_{AHPND}$ can be directly determined, significantly reducing detection time.

In summary, the melting curve-based multiplex fluorescent quantitative primer set and detection method developed in this invention enables rapid, simple, and sensitive detection of EHP, DIV1, IHHNV, WSSV, and $V_{AHPND}$ with high specificity and accuracy. This approach is particularly advantageous for large-scale screening in aquaculture, offering a robust solution for timely pathogen identification and disease management.

What is claimed is:

1. A detection method of multiplex fluorescent quantitative detection method for simultaneous qualitative and quantitative detection of multiple pathogens, wherein, the detection method is non-diagnostic and non-therapeutic, wherein the detection method is applied in rapid pathogen detection in aquatic animals; the pathogens are *Enterocytozoon hepatopenaei*, (EHP), Decapod iridescent virus 1, (DIV1), infectious hypodermal and hematopoietic necrosis virus, (IHHNV), white spot syndrome virus, (WSSV), and acute hepatopancreatic necrosis disease causing *Vibrio*, ($V_{AHPND}$), the detection method comprises steps of:

(1) collecting samples and extracting genomic DNA as a template for fluorescent quantitative reactions, wherein a reaction system for fluorescent quantitative PCR has a total volume of 25 μL, and the reaction system comprises 2×dsDNA-binding fluorescent dye premix containing 50 U/μL Taq DNA polymerase, 2 mM dNTPs, 50× 5-carboxy-X-rhodamine reference dye, dsDNA-binding fluorescent dye, 20 mM Tris-HCl, 0.1 mM EDTA, 100 mM NaCl, 0.5% polysorbate 20, 1 mM dithiothreitol, 50% volume ratio of glycerol: 12.5 μL; primers: 0.56 μM of EHP-2-F, 0.56 μM of EHP-2-R, 0.40 μM of IHHNV-P-3F, 0.40 μM of IHHNV-P-3R, 0.40 μM of WSSV-Y-2F, 0.40 μM of WSSV-Y-2R, 0.32 μM of DIV1-M-4F, 0.32 μM of DIV1-M-4R, 0.32 μM of VP-PB-3F, and 0.32 μM of VP-PB-3R; 1 μL of genomic DNA template; and deionized water being added to a total volume to 25 μL;

(2) mixing primers with dsDNA-binding fluorescent dye premix and the genomic DNA to form an amplification reaction system, then performing fluorescent quantitative amplification, wherein the amplification reaction system was loaded into a real-time PCR instrument, and the fluorescent quantitative reaction conditions are: 95° C. for 3 minutes, 40 cycles of 95° C. for 10 seconds and 64° C. for 20 seconds;

(3) after amplification, analyzing melting curves to determine the presence of EHP, DIV1, IHHNV, WSSV, and $V_{AHPND}$ in the samples, wherein the analyzing melting curves was conducted at 95° C. for 15 seconds, and 64° C. for 1 minute, and melting curve data was collected at 68° C. to 85° C.;

wherein the method further comprises constructing recombinant plasmids containing gene sequences corresponding to a SWP protein of EHP, a MCP protein of DIV1, a NS1 protein of IHHNV, a WSV313 protein of WSSV, and a PirB protein of $V_{AHPND}$;

wherein sequences of the primers are SEQ ID NOs.: 1-10.

2. The detection method according to claim 1, wherein analysis of amplification curves is performed as follows: test is valid only if: negative controls show no amplification curves, positive controls exhibit amplification curves with Cycle Threshold, (Ct) values less than or equal to 37, otherwise, the test is invalid and must be repeated, a sample with Ct less than or equal to 37 is positive for the pathogens, for samples with 37 less than Ct less than or equal to 40 retest with 2.5 μL of template DNA; when the retested sample shows an amplification curve with Ct less than or equal to 37, the result is positive; otherwise, it is negative, samples with no amplification curves are negative.

3. The detection method according to claim 1, wherein melting curve analysis is performed as follows: a single peak matching a Tm value of the EHP-positive control confirms EHP; a single peak matching a melting temperature (Tm) value of the WSSV-positive control confirms WSSV; a single peak matching a Tm value of the $V_{AHPND}$-positive control confirms $V_{AHPND}$; a single peak matching a Tm value of the IHHNV-positive control confirms IHHNV; a single peak matching a Tm value of the DIV1-positive control confirms DIV1; multiple peaks corresponding to Tm values of specific positive controls indicate co-infection; no peaks indicate the sample is negative for all five pathogens.

4. A primer set for simultaneous qualitative and quantitative detection of EHP, DIV1, IHHNV, WSSV, and $V_{AHPND}$; wherein sequences of the primer set are SEQ ID NOs. 1-10;

wherein the primer set is configured to be used in the detection method according to claim 1 and applied in rapid pathogen detection in aquatic animals.

5. A detection kit of multiplex fluorescent quantitative PCR for simultaneous qualitative and quantitative detection of multiple pathogens, wherein the detection kit comprises the primer set according to claim 4.

* * * * *